(12) United States Patent
Young

(10) Patent No.: US 10,667,926 B2
(45) Date of Patent: Jun. 2, 2020

(54) FEMORAL IMPLANT REVISION TOOL

(71) Applicant: ORTHOFIX S.R.L., Milan (IT)

(72) Inventor: Michael Young, Ashburton (GB)

(73) Assignee: ORTHOFIX S.R.L., Milan (IT)

( * ) Notice: Subject to any disclaimer, the term of this patent is extended or adjusted under 35 U.S.C. 154(b) by 368 days.

(21) Appl. No.: 14/928,734

(22) Filed: Oct. 30, 2015

(65) Prior Publication Data

US 2016/0051378 A1    Feb. 25, 2016

Related U.S. Application Data

(63) Continuation of application No. 13/825,589, filed as application No. PCT/GB2011/001376 on Sep. 21, 2011, now Pat. No. 9,198,776.

(30) Foreign Application Priority Data

Sep. 22, 2010   (GB) .................................. 1015998.6

(51) Int. Cl.
*A61F 2/46* (2006.01)
*A61B 17/22* (2006.01)
*A61B 17/16* (2006.01)
*A61B 17/32* (2006.01)
*A61F 2/30* (2006.01)

(52) U.S. Cl.
CPC ........ *A61F 2/4607* (2013.01); *A61B 17/1604* (2013.01); *A61B 17/22004* (2013.01); *A61B 2017/320075* (2017.08); *A61B 2017/320078* (2017.08); *A61F 2002/30067* (2013.01); *A61F 2002/3082* (2013.01); *A61F 2002/30131* (2013.01); *A61F 2002/30879* (2013.01);
(Continued)

(58) Field of Classification Search
CPC ......... A61B 2017/22014; A61B 2017/320072; A61B 2017/320076; A61B 17/22004; A61B 17/22012; A61B 17/1604; A61B 17/1659; A61B 17/1642; A61B 17/320068; A61F 2/4607; A61F 2002/4609; A61F 2002/4619; A61F 2002/4683
USPC ............................................... 606/79, 84–85
See application file for complete search history.

(56) References Cited

U.S. PATENT DOCUMENTS 5,318,570 A * 6/1994 Hood ................. A61B 17/8847
601/2
6,022,217 A * 2/2000 Hugo ....................... A61C 3/03
433/119
(Continued)

*Primary Examiner* — Christian A Sevilla
*Assistant Examiner* — Tracy L Kamikawa
(74) *Attorney, Agent, or Firm* — Cook Alex Ltd.

(57) ABSTRACT

An osteotome suitable for cutting through cancellous bone that is holding an orthopaedic implant requiring revision within a cavity of a bone, comprises a cylindrical waveguide connectable to a source of ultrasonic vibrations at its proximal end and a blade having a hollow part-cylindrical cross-section and a cutting edge at its distal tip. The respective longitudinal axes of the waveguide and the blade cross at an angle of about 30°, and the waveguide and blade taper and curve smoothly together where they meet. The osteotome is dimensioned such that a first antinode of the ultrasonic vibrations is located at a proximal end of the waveguide, a second antinode is located at the distal tip of the blade and a node is located where the waveguide and blade meet. The osteotome cuts readily through cancellous bone when ultrasonically energized.

15 Claims, 7 Drawing Sheets

(52) U.S. Cl.
CPC .............. *A61F 2002/4619* (2013.01); *A61F 2002/4683* (2013.01)

(56) References Cited

U.S. PATENT DOCUMENTS

| | | | |
|---|---|---|---|
| 6,204,592 B1* | 3/2001 | Hur .................... | A61B 17/1624 310/323.12 |
| 6,241,703 B1* | 6/2001 | Levin ............... | A61B 17/22012 604/22 |
| 6,432,118 B1* | 8/2002 | Messerly ....... | A61B 17/320092 606/169 |
| 2008/0234710 A1* | 9/2008 | Neurohr ......... | A61B 17/320068 606/169 |
| 2011/0278988 A1* | 11/2011 | Young ............ | A61B 17/320068 310/328 |
| 2012/0141744 A1* | 6/2012 | Ambroise ............... | B32B 27/32 428/195.1 |

* cited by examiner

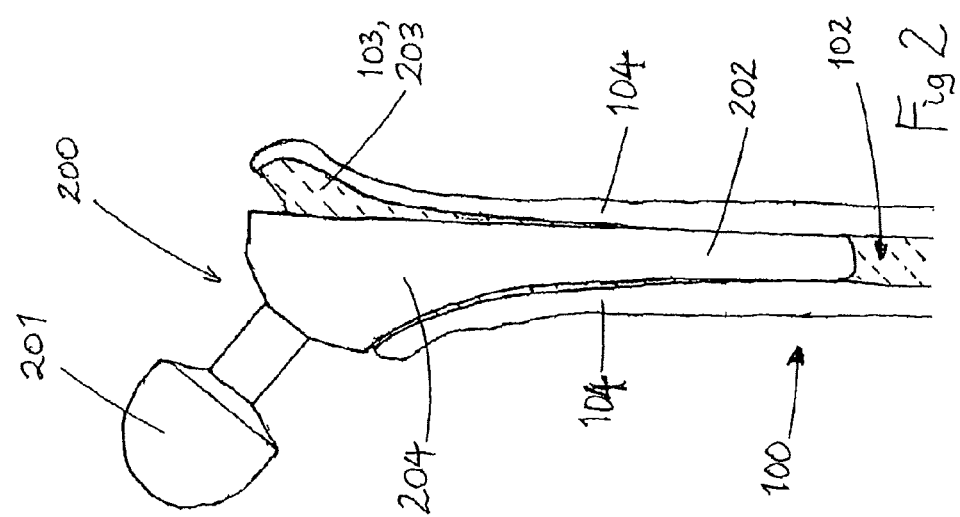
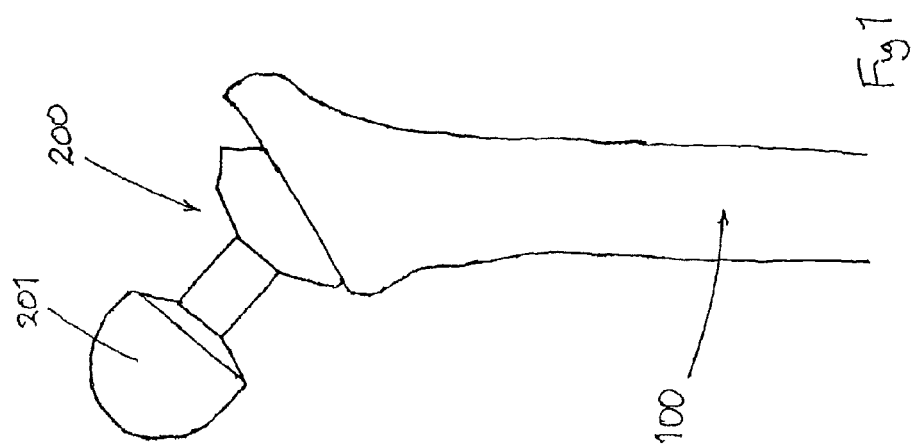

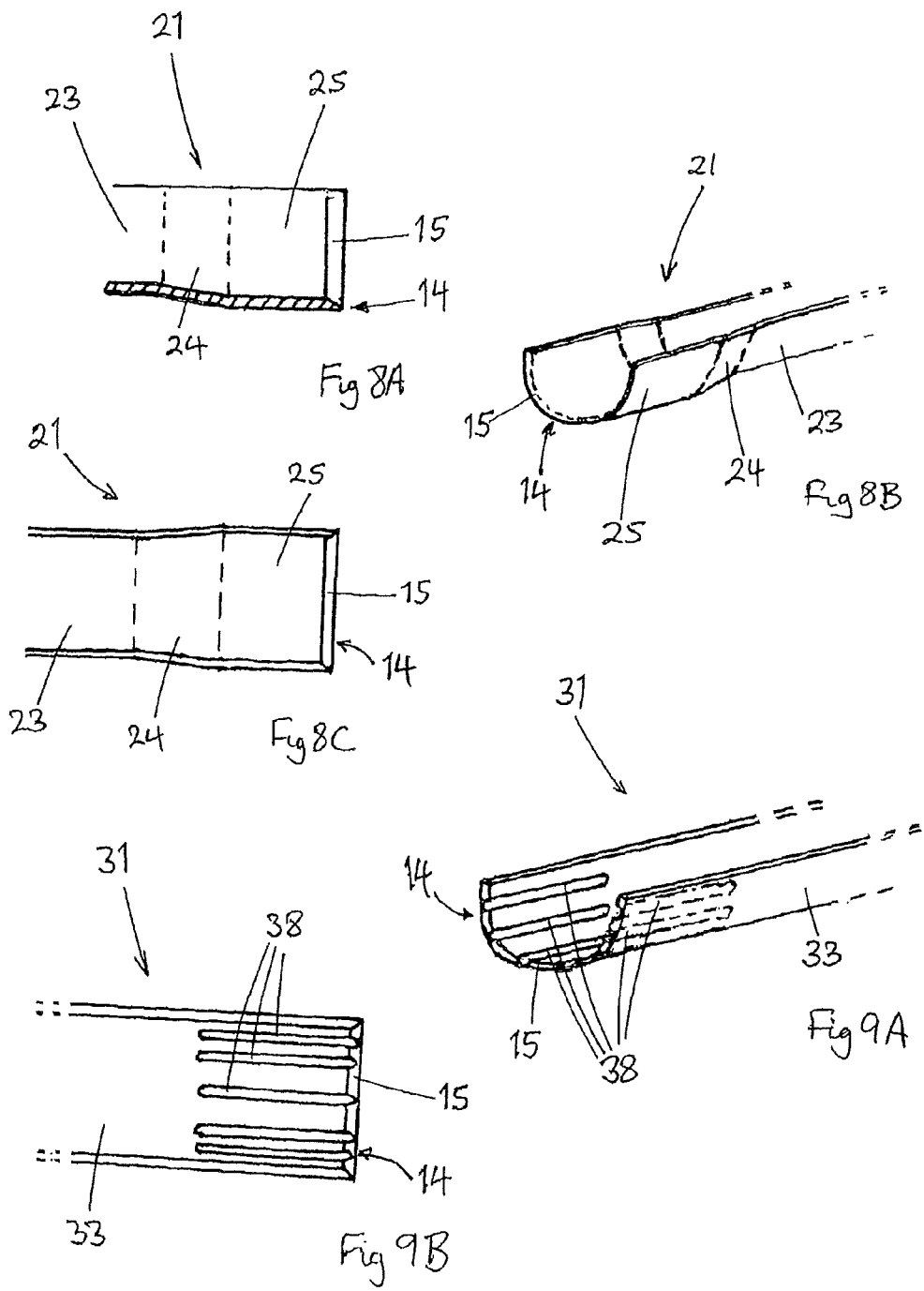

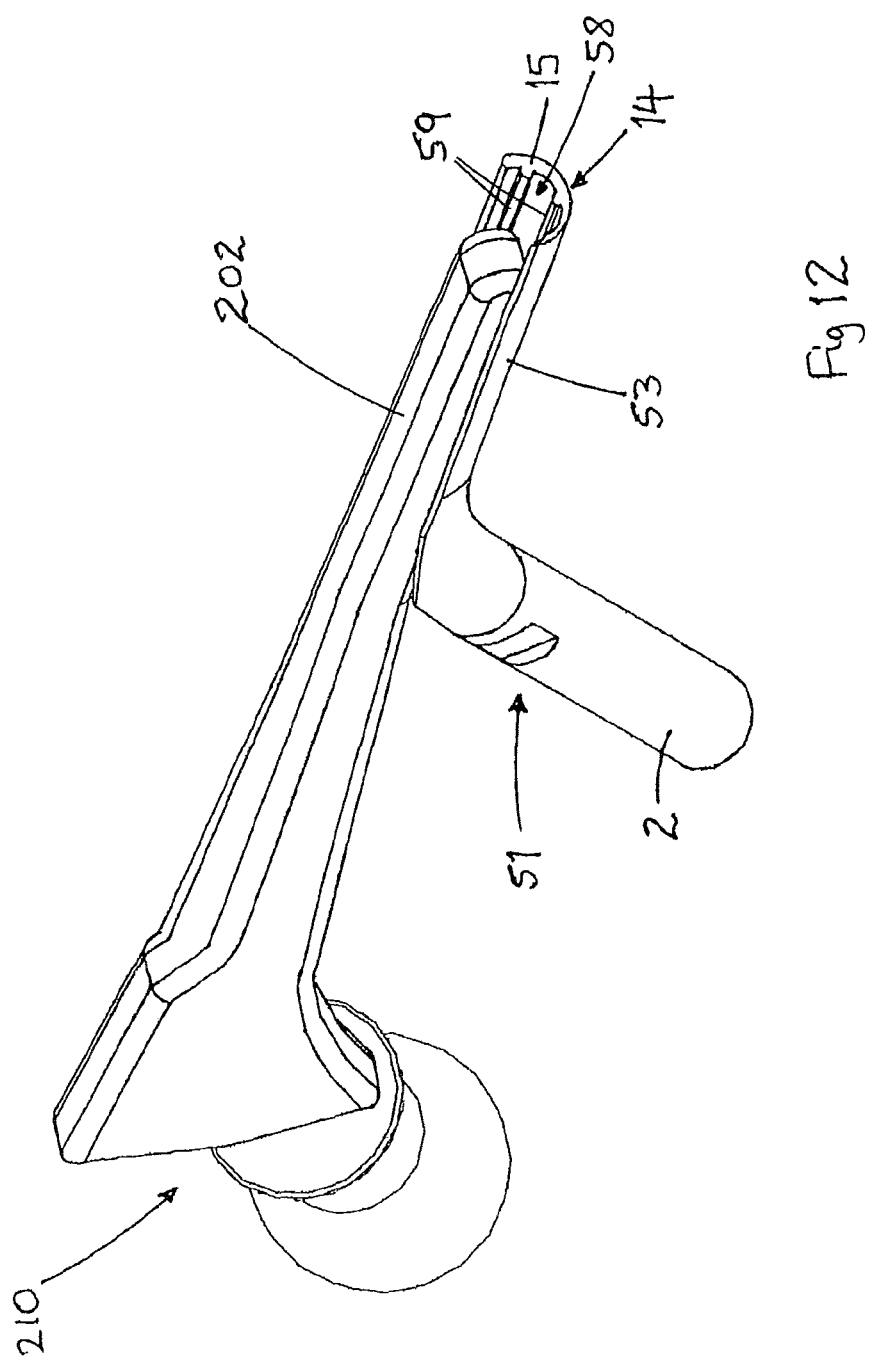

FEMORAL IMPLANT REVISION TOOL

This application is a continuation of U.S. patent application Ser. No. 13/825,589, filed Apr. 23, 2013, currently pending.

The present invention relates to a surgical implement suitable for use in the revision of orthopaedic prosthetic implants. More particularly but not exclusively, it relates to an ultrasonically-vibratable surgical implement for removing a stem of a hip joint prosthesis embedded within a femur.

Orthopaedic joint replacements, such as hip joint prostheses, generally have service lives of fifteen to twenty years. However, with human lifespans increasing, this means that many patients with such implants will experience problems requiring revision of the prosthesis, i.e. its removal and replacement. Prostheses may eventually fracture as a result of simple metal fatigue or overstressing. Other problems include wear and damage to the "ball and cup" elements that articulate the portion of the prosthesis implanted in the femur to the portion of the prosthesis mounted to the pelvis. If resulting polymer and metal fragments enter body tissues, they may cause an immune reaction, as the body attempts to absorb them. Absorption is not possible, but the immune reaction may meanwhile locally destroy existing bone material. Another problem arises if the implant in the femur starts to come loose, which may cause severe pain and inflammation, as well as locally weakening the surrounding bone.

It is therefore important to be able to remove an orthopaedic implant from a femur or other bone while causing minimal damage to surrounding bone material, thus facilitating implantation of the new implant and aiding subsequent healing. A femoral implant typically has an elongate stem which is inserted into the cavity or channel of the shaft of the femur, the ball of the articulation being mounted to the proximal end of the stem. The stem may be secured within the shaft of the femur using a polyacrylate cement (a "cemented" implant) or it may be provided with a textured surface to encourage ingrowth of cancellous bone to anchor the stem in place (an "uncemented" implant).

It is known to use ultrasonically-vibratable tools to soften the cement holding cemented implants in place, allowing relatively rapid and straightforward subsequent extraction of the implant. However, to remove uncemented implants, a surgeon must directly cut away the cancellous bone that has formed between an inner surface of the channel of the femur and the stem of the implant, before the implant can be extracted. This is currently a lengthy and difficult procedure.

Typically, a proximal section of the wall of the femur is cut open and temporarily hinged back to provide lateral access to an upper part of the stem of the implant. A wire saw is passed behind the implant and is moved down the stem, gradually sawing away the cancellous bone encircling the stem. However, the approach of cutting through the bone to access the stem cannot be used all the way down the stem, or the femur could be permanently weakened. The cancellous bone around a distal portion of the stem must therefore be dealt with by alternative methods. In principle, an osteotome blade might be inserted down between the stem and the bone of the shaft, to chisel away the cancellous bone. However, the required direction of approach of the blade is usually hampered by the proximal portion of the implant. A surgeon may therefore first need to saw through the stem of the implant and remove the proximal portion, before chiselling out a remaining stub of the distal portion of the stem, or cutting around the stub with a trephine. The implant typically comprises a hard cobalt steel, so sawing through it is slow, wears away saw blades rapidly, and creates a great deal of metal swarf, which must be kept away from soft tissues of the body.

Such a prolonged procedure may be harmful to the patient, who must be kept under general anaesthetic throughout. Many patients requiring such a procedure will be in imperfect health, making prolonged anaesthesia risky. Additionally, during such lengthy and labor intensive procedures, there is a risk of fatigue and impaired performance on the part of the surgeon.

It is hence desirable that an alternative approach be devised for cutting away cancellous bone that has formed between an elongate stem of a femoral implant (or other long bone implant) and an inner surface of the shaft of the femur (or other long bone). Such an approach should ideally be quicker, less labor-intensive, more precise and more convenient than existing approaches.

It is hence an object of the present invention to provide a surgical tool, suitable for cutting cancellous bone around an orthopaedic implant in situ, which obviates the above disadvantages and provides some or all of the above benefits.

According to a first aspect of the present invention, there is provided a cutting element for an ultrasonically-vibratable surgical tool, comprising elongate waveguide means mountable adjacent its proximal end to a source of ultrasonic vibrations and having elongate blade means extending from adjacent its distal end, wherein a longitudinal axis of the waveguide means and a longitudinal axis of the blade means intersect at an acute non-zero angle.

Preferably, the blade means comprises a cutting edge at its distal tip.

The cutting element may comprise an osteotome element.

The cutting element may be adapted to cut cancellous bone, optionally cancellous bone retaining orthopaedic implant means within a lumen of a bone.

In a preferred embodiment, the blade means has an arcuate cross-sectional profile.

The blade means may have a constant cross-sectional profile along at least a majority of its length.

The blade means advantageously comprises a portion of an elongate hollow cylinder.

A distal portion of the blade means may have a cross-sectional profile greater in diameter than a remainder thereof.

A distal portion of the blade means may be provided with at least one longitudinal groove means extending along a concave face thereof.

In a preferred embodiment, the blade means is provided on a face thereof adjacent its distal tip with spacing means adapted to contact a substrate surface to guide the blade means.

The spacing means thus prevents direct contact between said face of the blade means and said substrate surface.

The spacing means may be provided on a concave face of a blade means having an arcuate cross-sectional profile.

The spacing means may comprise a layer of thermoplastics material, optionally a fluoropolymer, a polyether ether ketone or a high density polyalkene.

The spacing means may alternatively or additionally comprise a plurality of rib means upstanding from said face of the blade means.

Said rib means may extend substantially longitudinally of the blade means.

Preferably, a thickness of the blade means is significantly lower than a thickness of the waveguide means.

Advantageously, a profile of the waveguide means and a profile of the blade means blend smoothly adjacent their junction.

The cutting element may comprise a curved junction region including a distal end of the waveguide means and a proximal end of the blade means.

The waveguide means may comprise an elongate solid cylindrical body.

Preferably, said angle between the respective longitudinal axes of the waveguide means and the blade means is between 10° and 45°.

Advantageously, said angle is between 25° and 35°, optionally approximately 30°.

Preferably, the cutting element has an overall length of approximately $(2n+1) \lambda/2$, where n is a positive integer and $\lambda$, is a wavelength of an ultrasonic vibration within the material of the cutting element.

Optionally, the cutting element may have an overall length of approximately $3\lambda/2$.

Advantageously, the waveguide means has a length of approximately $(2n+1) \lambda/4$.

Optionally, the waveguide means may have a length of approximately $3\lambda/4$.

The blade means may have a length of approximately $(2m+1) \lambda/4$, where m is a positive integer.

Optionally, the blade means may have a length of approximately $3\lambda/4$.

The blade means and the waveguide means may each have a length of $(2n+1) \lambda/4$.

Optionally, the blade means and the waveguide means may each have a length of approximately $3\lambda/4$.

Preferably, the cutting element is so configured that when vibrated by said source of ultrasonic vibrations, a first antinode of the ultrasonic vibrations is located adjacent a proximal end of the waveguide means, a second antinode of the ultrasonic vibrations is located adjacent a distal tip of the blade means and a node of the ultrasonic vibrations is located adjacent a junction of the waveguide means and the blade means.

Advantageously, the cutting element is so configured that said ultrasonic vibrations undergo a gain in amplitude across the junction of the waveguide means and the blade means.

The source of ultrasonic vibrations preferably comprises a source of longitudinal-mode ultrasonic vibrations.

The cutting element is advantageously so mountable to the source of ultrasonic vibrations that said longitudinal mode ultrasonic vibrations are directed substantially parallelly to the waveguide means.

According to a second aspect of the present invention, there is provided a surgical tool comprising a cutting element as described in the first aspect above, operatively connected to a source of ultrasonic vibrations.

Preferably, said source of ultrasonic vibrations comprises a source of longitudinal-mode ultrasonic vibrations.

According to a third aspect of the present invention, there is provided a method of separating a stem of an orthopaedic implant from surrounding bone, comprising the steps of providing a surgical tool having a cutting element as described in the first aspect above, applying blade means thereof to a region between an inner surface of a cavity in a bone and a stem of an orthopaedic implant embedded in said cavity, and causing the cutting element to vibrate at an ultrasonic frequency so as to sever bonding material extending within said region.

Said bonding material may comprise cancellous bone.

Said bonding material may comprise a polymeric cement composition.

Embodiments of the present invention will now be more particularly described by way of example and with reference to the accompanying drawings, in which;

FIG. 1 is a frontal elevation of an upper portion of a femur with a first implant in place;

FIG. 2 is a longitudinal cross-sectional view of the femur of FIG. 1, showing the location of a stem of the first implant within the femur;

FIG. 8A is a scrap longitudinal cross-sectional elevation of a distal portion of a second cutting tool embodying the present invention;

FIG. 8B is a scrap perspective view of the distal portion of the tool of FIG. 8A;

FIG. 8C is a scrap plan view from above of the distal portion of the tool of FIG. 8A;

FIG. 9A is a scrap perspective view of a distal portion of a third cutting tool embodying the present invention;

FIG. 9B is a scrap plan view from above of the distal portion of the tool of FIG. 9A;

FIG. 12 is a perspective view of the tool of FIG. 11 in operative alignment with a second femoral implant.

Figure 3:
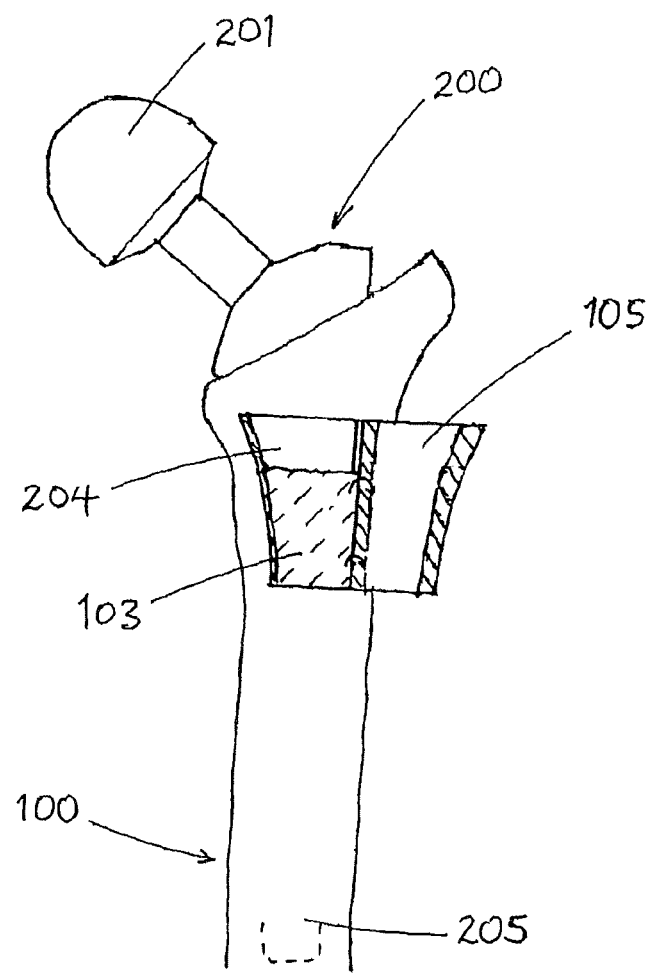
FIG. 3 is a frontal elevation of the femur of FIG. 1, part-way through a conventional revision procedure.

Referring now to the Figures, and to FIGS. 1 and 2 in particular, a human femur 100 is shown. In a previous surgical procedure, a first orthopaedic implant 200 has been implanted into the femur 100, such that a rounded head 201 of the first implant 200 replaces a head of the femur 100, and an elongate stem 202 of the first implant 200 is embedded in an elongate central cavity 102 of the femur 100.

A suitable surgical cement 203, normally a polyacrylate composition, may have been used to secure the first implant 200 in place. Alternatively, the first implant 200 may have been secured in place by the natural growth of cancellous bone 103, particularly between the stem 202 of the first implant 200 and the walls 104 of the shaft of the femur 100. In some cases, most or all of a surface of the stem 202 of the first implant 200 has a roughened surface, to which the cancellous bone 103 may "key". Other implants 200 have smaller roughened zones located on a proximal portion 204 of the stem 202 (although cancellous bone 103 will still adhere to non-roughened zones of the stem 202, albeit initially less strongly).

If any implant 200 becomes damaged or worn out, or begins to come loose, a revision procedure will be necessary to remove the existing implant 200 and replace it with another. It is hence necessary to separate the implant 200 from the femur, while leaving the femur 100 in a sufficiently sound condition to hold a replacement implant 200 securely.

Where the implant 200 is cemented, known ultrasonically-vibratable tools may be used to soften the cement 203 sufficiently for the implant 200 to be extracted, and further known ultrasonically-vibratable tools may be used to remove the remains of the cement 203, before the new implant 200 is cemented within the femur 100. This is usually a relatively rapid procedure, minimizing patient trauma and time spent under anaesthetic.

Currently, cutting away cancellous bone 103 is more difficult. Chiselling away cancellous bone 103 adjacent a proximal end of the stem 202 may be possible to a limited extent, but since the implant 200 is in situ, there is very little freedom of motion for conventional osteotomes because of surrounding tissues. It is therefore necessary, as shown schematically in FIG. 3, to cut open a "window" in the walls 104 of the femur 100, temporarily folding back a flap 105 of bone, so that the cancellous bone 103 may be approached laterally, freeing the proximal portion 204 of the stem 202. (NB the "window" may extend to a proximal rim of the walls 104 of the femur 100, when chiselling longitudinally from the open proximal end of the femur 100 is completely impractical). To sever cancellous bone 103 not directly accessible through this "window", a wire saw is passed behind the stem 202 and is used to saw down through this cancellous material.

Even though the flap 105 will be replaced after the procedure and will eventually heal and merge with the walls 104 of the femur 100, this weakens the femur 100, and this approach should not be used all the way down to a distal tip 205 of the stem 202. The window does not allow useful access to conventional osteotomes. It is usually necessary for the stem 202 to be sawn through, the proximal portion 204 to be removed, and then for the distal tip 205 to be chiselled out separately. The implant 200 generally comprises a hard cobalt steel, so sawing it through is a slow, labour intensive procedure, wearing away saw blades and creating metal fragments that must be prevented from entering body tissues.

Revision of an implant 200 can thus be a lengthy procedure, causing high levels of patient trauma and involving long periods under anaesthesia. It may also lead to manual fatigue on the part of the surgeon.

Figure 4:
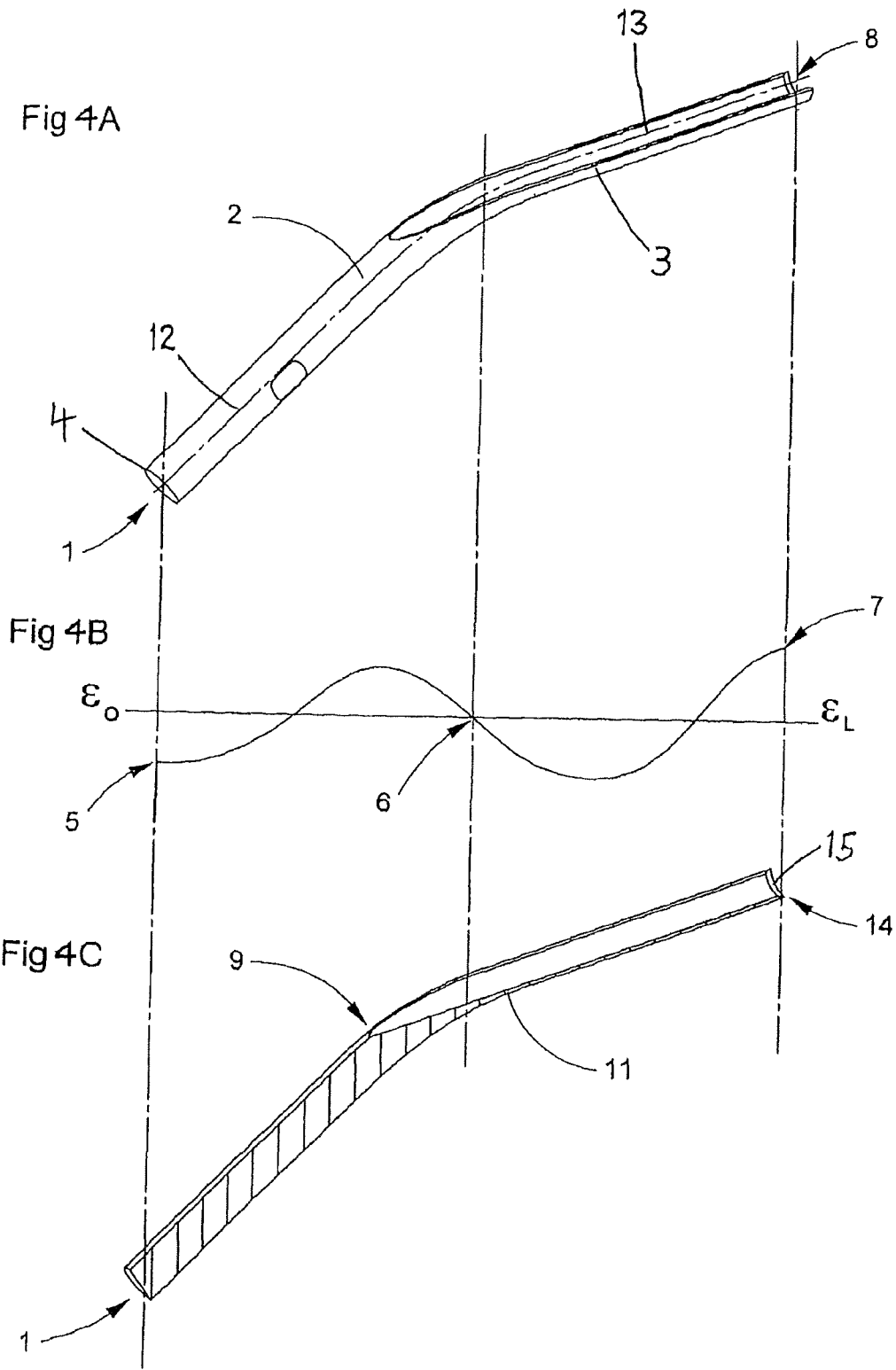
FIG. 4A is a perspective view of a first cutting tool embodying the present invention.
FIG. 4B is a schematic representation of a vibrational amplitude along the tool of FIG. 4A, in use.
FIG. 4C is a cross-sectional perspective view of the tool of FIG. 4A.

A first cutting tool or osteotome 1 embodying the present invention is shown in FIGS. 4A and 4C. The first tool 1 comprises an elongate cylindrical waveguide 2 having an elongate cutting blade 3 extending from a distal end of the waveguide 2. A proximal end 4 of the waveguide 2 is in practice fitted with a threaded connector or the like (here omitted for clarity), by which the tool 1 is connected to a source of ultrasonic vibrations, such as a longitudinal mode ultrasound generator of known form.

The cutting blade 3 has a substantially constant hollow semicircular profile (see also FIG. 5), and its distal tip 8 is provided with a bevel 15 leading to a relatively sharp distal cutting edge 14.

The blade 3 extends from the waveguide 2 at an angle; a longitudinal axis 12 of the waveguide 2 and a longitudinal axis 13 of the blade 3 intersect at an angle of 30° in this example, although this angle may vary while still producing an effective tool 1.

The waveguide 2 and blade 3 blend smoothly into each other across a curved joining zone 9. A concave face of the joining zone 9 has a smooth curved profile. However, a concave surface of the blade 3 continues as a groove extending straight across the joining zone 9 until it meets the waveguide 2 (see FIG. 4C). Thus, the thickness of the tool 1 tapers across the joining zone 9, the wall 11 of the blade 3 being substantially thinner than the cylindrical waveguide 2.

Ideally, the tool 1 may be formed from a single cylindrical stock piece of metal, which is first bent smoothly through a desired angle at the joining zone 9. The blade 3 is then machined out in a single straight pass. This creates the hollow semicircular profile of the blade 3 and the gradual taper across the joining zone 9, the groove becoming shallower and ending as the waveguide 2 curves away beneath it.

The tool 1 shown is devised to be used with longitudinal-mode ultrasonic vibrations of a known frequency, and hence a known wavelength in a given material (to a first approximation at least).

As shown in FIG. 4B, the waveguide 2 in this case has a length of approximately three-quarters of the wavelength of the ultrasonic vibrations therein. The source of ultrasonic vibrations is connected to the waveguide 2 at its proximal end 4, such that there is a first anti-node 5 in the vibrations at this point. The length of the waveguide 2 produces a nodal point 6 in the vibrations, located within the joining zone 9. The blade 3 also has a length of three-quarters of the wavelength of the ultrasonic vibrations therein. Thus, there will be a second anti-node 7 at the distal tip 8 of the blade 3.

It is found that with the profile of the joining zone 9 shown, there is a remarkably good transmission of energy "around the bend" in the tool 1, from the waveguide 2 to the blade 3. Additionally, the reduction in the cross-sectional area of the tool 1, from the cylindrical waveguide 2 to the thin semi cylindrical walls 11 of the blade 3, produces a gain in the amplitude of the vibrations. Across an abrupt step in the diameter of the tool, the gain is a function of the ratio of the cross sectional areas each side of the step. Across a more gradual change in cross-sectional area, as in this tool 1, it is found that a similar gain can be achieved.

As a result, this tool 1 may be energized with longitudinal-mode ultrasonic vibrations to produce a reciprocal motion of the distal cutting edge 14, directed parallel to the longitudinal axis 13 of the blade, with an amplitude of at least 60 micrometers.

This motion, applied to cancellous bone 103, is easily sufficient to chisel it away without requiring a user to do more than apply the distal tip 8 to the cancellous bone and activate the ultrasonic vibrations. (It should also cut through bone cement 203 with ease).

Figure 5:
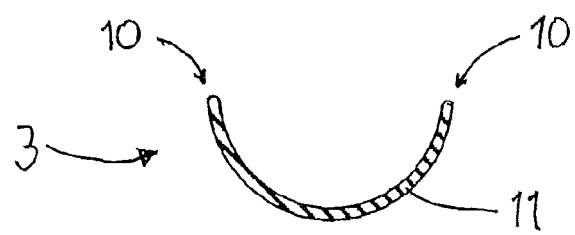
FIG. 5 is a transverse cross-section of a blade of the tool of FIG. 4A.
Figure 6:
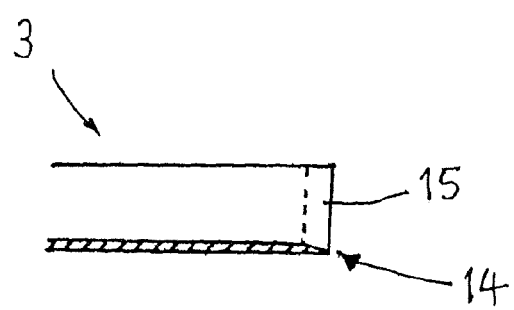
FIG. 6 is a scrap longitudinal cross-sectional elevation of a distal portion of the tool of FIG. 4A.

FIGS. 5 and 6 show preferred features of the blade 3. Since the blade 3 is likely to contact the stem 202 of an implant 200 or surrounding tissues in use, it is preferred that each lateral rim 10 of the blade 3 should be rounded smoothly, rather than being left with rougher or sharply-angled edges. This should reduce the risk of damage to the blade 3, especially since some implants 200 have roughened surfaces.

FIG. 6 shows how the bevel 15 is preferably formed on an inner, concave face of the blade 3, defining a sharper distal cutting edge 14. This need not necessarily be as sharp as that of a conventional hand-impelled osteotome, but it should be significantly sharper than any other edge or rim on the tool 1, such that it is safe when not energized, and the only significant cutting element when the tool 1 is energized.

Figure 7:
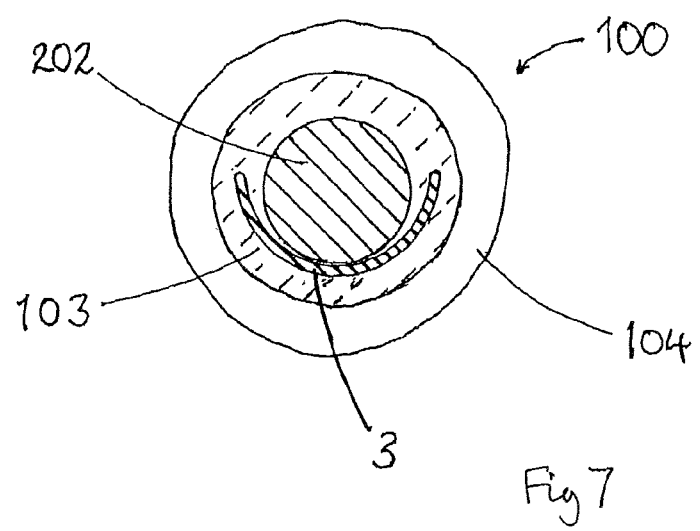
FIG. 7 is a schematic transverse cross-section of the tool of FIG. 4A in use.

FIG. 7 shows, in schematic form, the first tool 1 in use (some relative sizes and proportions have been adjusted for clarity, rather than strict accuracy). In this example, a stem 202 of an implant 200 is held within the wall 104 of a femur 100 by cancellous bone 103 (the thickness of which is exaggerated in this Figure). The tool 1 is aligned such that the longitudinal axis of the blade 3 is directed substantially in parallel to the longitudinal axis of the stem 202. To guide the blade 3, a concave face of the blade 3 may be contacted with the stem 202 and the blade 3 may then be run down the stem 202. This should keep the blade 3, and the rims 10 of blade 3 in particular, away from the walls 104 of the femur 100. The osseous bone of the walls 104 would be more resistant to cutting than the cancellous bone 103, but any unnecessary damage to the osseous bone should be avoided. The user is then able to press the blade 3 smoothly down the stem 202, the distal cutting edge 14 cutting through the cancellous bone 103 as it goes. Very little force should be needed once the tool 1 is ultrasonically vibrated. Only a limited number of passes would be required to isolate the stem 202 from the surrounding cancellous bone 103, particularly when the curvature of the blade 3 is matched closely to that of the stem 202 (unlike in FIG. 7, where the differences in radius of curvature are exaggerated for effect).

The curve of the joining zone 9 of the tool 1 allows the blade 3 to be presented at the correct angle to be used as described above, while the waveguide 2 and a remainder of the tool 1 mounted thereto are conveniently canted away from surrounding tissues. A manually-impelled osteotome with such a geometry would be difficult to impel longitudinally of the femur 100, but the discovery that ultrasonic vibrations may be transmitted reliably and controllably around a curve in mid-tool (with a gain in amplitude into the bargain) allows the ultrasonically-vibratable tool 1 of the present invention to cut with minimal force and maximal convenience.

The tool 1 may conveniently be used with longitudinal-mode ultrasound generators operating at between 20 kHz and 60 kHz, which are already used in a range of surgical tools. Since the optimal length of the tool 1 depends on the wavelength of the vibrations produced in the tool 1, it would be possible to produce tools of a range of desired dimensions, each achieving resonance at the exact frequency that puts a node in the joining zone 9 and an anti-node at the distal tip 8.

FIGS. 8A to 9B, show two variant forms of tool embodying the present invention. It may be beneficial to profile the blade to allow easier passage of cut debris away from the cutting edge. In a second cutting tool 21 (FIGS. 8A and 8C), a majority of the blade 23 has a constant profile, but adjacent a distal end it comprises a coaxially-extending section 25 of greater diameter, joined to the main blade 23 by a flaring section 24.

Ultrasonically-vibrated tools can cause significant local heating in use. In a third cutting tool 31 (FIGS. 9A, 9B), a series of parallel longitudinal grooves 38 are formed along a distal section of the blade 33, extending across the bevel 15 to the cutting edge 14. These allow cooling water to be delivered down the blade 33 to the cutting edge 14.

While in each of the tools 1, 21, 31 illustrated, the bevel 15 is shown in the inner, concave surface of the blade 3, 23, 33, it would also be possible to bevel the outer, convex surface if desired.

Figure 10:
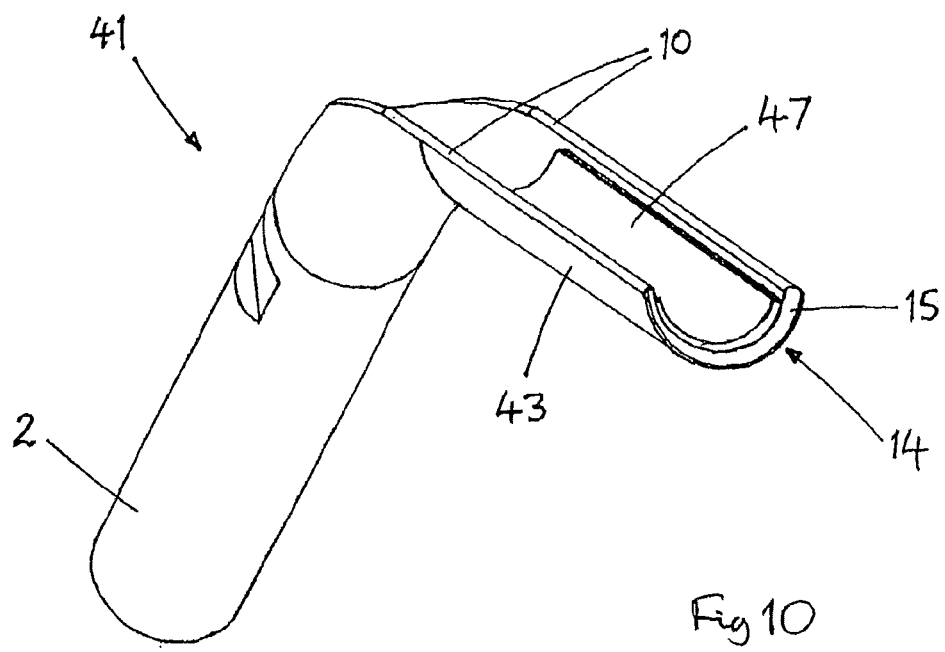
FIG. 10 is a perspective view of a fourth cutting tool embodying the present invention.
Figure 11:
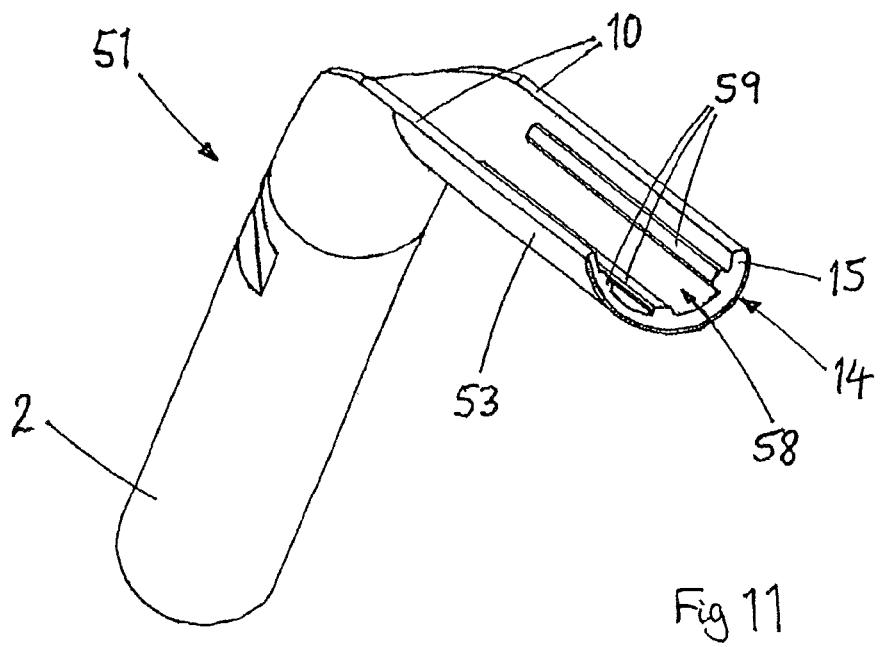
FIG. 11 is a perspective view of a fifth cutting tool embodying the present invention.

Although running the concave surface of the blade 3 down the stem 202 of an implant 200 guides the blade 3 with the required accuracy, it has been found in trials that prolonged contact between the blade 3 and the stem 202, particularly over large contact areas, may lead to fatigue problems in the metal of the blade 3. FIGS. 10 and 11 show two improvements to the blade 3 that help to obviate this problem.

FIG. 10 shows a fourth tool 41 embodying the present invention, which is similar in most respects to the first tool 1. There is an elongate cylindrical waveguide 2, connectable to a source of ultrasonic vibrations, with an elongate blade 43 extending from its distal end. At a distal end of the blade 43, a bevel 15 leads to a distal cutting edge 14.

As in the case of the blades 3, 23, 33 above, this blade 43 has towards its distal tip a thin-walled part-circular cross-section. The lateral rims 10 of the hollow part-cylindrical profile thus formed are again rounded-off.

In order to obviate metal fatigue resulting from contact between the ultrasonically-vibrated, concave face of the titanium blade 43 and the cobalt steel stem 202, the concave face of the blade 43 is provided with a lining or insert 47 of poly (tetrafluoroethylene), polyether ether ketone, high density polyethylene (i.e. PTFE, PEEK or HDPE), or other thermoplastics material having a degree of resilience, mechanical integrity and low coefficient of friction. This lining 47 extends proximally from immediately adjacent the bevel 15 along a major portion of the blade 43, and it conforms to the profile of the concave face of the blade 43, having a substantially constant thickness. (Instead of a lining 47, a coating of PTFE or the like could also be applied to this concave surface). As such, the lining 47 shown in FIG. 10 provides a spacer between the blade 43 and the stem 202 of the implant 200.

In use, when this blade 43 is brought up to a stem 202, only the insert 47 will contact the stem 202. As the blade 43 is passed down the stem 202, there will be minimal vibrating metal-metal contact and hence minimal risk of metal fatigue.

FIG. 11 shows a fifth tool 51 embodying the present invention, which employs a different approach. The fifth tool 51 again has most of the features of the first tool 1, including an elongate blade 53 extending from a distal end of an elongate cylindrical waveguide 2 to a terminal bevel 15 and a distal cutting edge 14. This blade 53 again has a thin-walled part-circular cross-section towards its distal tip, with rounded off lateral rims 10 to the hollow, part-cylindrical profile thus formed.

The blade 53 of the fifth tool 51 is also provided with a set of longitudinally-extending upstanding ribs or fins 59, spaced around its concave face. The fins 59 extend proximally from the bevel 15 (a distal end of each fin 59 may, as shown, continue the bevelled profile) along a major portion of the blade 51. Each fin is radially upstanding to a constant height above the concave face of the blade 51. In a similar manner to the lining 47, the fins 59 shown in FIGS. 11 and 12 provide a spacer between the blade 53 and the stem 202 of the implant 200.

Thus, when this blade 53 is brought into contact with a stem 202 of an implant 200, and as the blade 53 is passed down to stem 202, the blade 53 and stem 202 will only be in contact along an upper surface of the fins 59.

FIG. 12 shows the fifth tool 51 in operative alignment with the stem 202 of a second femoral implant 210, to demonstrate this point (the second femoral implant 210 has minor differences of detail, compared to the first 200, but its stem 202 is substantially identical). The stem 202 is almost cradled within the part-cylindrical profile of the blade 53, contacting the blade 53 only along the upper surface of each fin 59. The blade 53 can thus pass freely along the stem 202 as it cuts through the cancellous bone 103 surrounding the stem 202.

Because the contact area between the fins 59 and the stem 202 is so small, any metal fatigue in the blade 53 will be localized within the fins 59. Even if there is localized damage to a fin 59, this would have little effect on the performance of the tool 51 as a whole.

As can be seen from FIGS. 11 and 12, the upstanding longitudinal fins 59 along the inner, concave face of the blade 53 could be considered to define channels 58 between them. These could be used to pass cooling water down the blade 53 to its distal cutting edge 14 (as for the grooves 38 of the third tool 31), and/or could provide convenient passage away from the cutting edge 14 for fragmentary debris created as the cutting edge 14 passes through cancellous bone 103.

In the particular example of the fifth tool 51 shown, the fins 59 are formed integrally with the blade 53 as the tool 51 is machined into shape. In a variant (not shown) the fins 59 are instead formed as part of a pre-formed insert or lining, e.g. of PTFE, PEEK or the like, mounted to the inner, concave surface of the blade 53.

It is also possible to form circumferentially-extending upstanding fins on the inner, concave face of the blade 51, which would also produce the same stand-off function to obviate metal fatigue in the operative portions of the blade 53. In this variant, the fins would not define longitudinal channels for passage of debris and/or cooling water, and might be slightly less convenient for longitudinal motion, but the tool should still be superior to a tool 1 with a plain concave surface leading to extensive vibrating metal-metal contact. Either should be far superior to existing tools and methods described above.

The invention claimed is:

1. A cutting element for an ultrasonically-vibratable surgical tool, comprising an elongate waveguide having a cylindrical shape from a proximal end to a distal end, the waveguide being mountable adjacent the proximal end to a source of ultrasonic vibrations and having an elongate blade having a hollow part-cylindrical shape from a proximal end to a distal end and extending along a longitudinal axis from the proximal end of the blade to the distal end of the blade, with the blade extending from a joining region at the distal end of the waveguide, wherein a longitudinal axis of the waveguide and the longitudinal axis of the blade intersect at an acute non-zero angle, and wherein the cylindrical shape and part-cylindrical shape have substantially the same radius of curvature, and further comprising a spacer attached directly to a face of the blade with the spacer adapted to contact a stem of an implant to prevent direct contact between said face of the blade and the stem of the implant.

2. The cutting element as claimed in claim 1, wherein the blade comprises a distal tip having a cutting edge.

3. The cutting element as claimed in claim 1, wherein the blade has an arcuate cross-sectional profile.

4. The cutting element as claimed in claim 1, wherein the face of the blade to which the spacer is attached is concave.

5. The cutting element as claimed in claim 1, wherein the spacer comprises a layer of thermoplastics material.

6. A cutting element as claimed in claim 1, wherein the spacer comprises a plurality of ribs upstanding from said face of the blade.

7. A cutting element as claimed in claim 6, wherein said ribs extend substantially longitudinally of the blade.

8. The cutting element as claimed in claim 1, wherein a thickness of the blade is significantly lower than a thickness of the waveguide.

9. The cutting element as claimed in claim 1, wherein a profile of the waveguide and a profile of the blade blend smoothly along the joining region.

10. The cutting element as claimed in claim 1, wherein said angle between the respective longitudinal axes of the waveguide and the blade is between 10° and 45°.

11. The cutting element as claimed in claim 10 wherein said angle between the respective longitudinal axes of the waveguide and the blade is approximately 30°.

12. The cutting element as claimed in claim 1, wherein the cutting element further comprises a material and has an overall length of approximately $(2n+1)\lambda/2$, where n is a positive integer and $\lambda$ is a wavelength of an ultrasonic vibration within the material of the cutting element.

13. The cutting element as claimed in claim 1, wherein the cutting element further comprises a material and the waveguide has a length of approximately $(2n+1)\lambda/2$, $\lambda/4$, where n is a positive integer and $\lambda$ is a wavelength of an ultrasonic vibration within the material of the cutting element.

14. The cutting element as claimed in claim 1, so configured that when vibrated by said source of ultrasonic vibrations, a first antinode of the ultrasonic vibrations is located adjacent the proximal end of the waveguide, a second antinode of the ultrasonic vibrations is located adjacent a distal tip of the blade and a node of the ultrasonic vibrations is located adjacent the joining region.

15. A surgical tool comprising:
a source of ultrasonic vibrations;
a cutting element operatively connected to the source of ultrasonic vibrations and comprising an elongate waveguide having a cylindrical shape from a proximal end to a distal end, the waveguide being mounted adjacent the proximal end to the source of ultrasonic vibrations and having an elongate blade having a hollow part-cylindrical shape from a proximal end to a distal end and extending along a longitudinal axis from the proximal end of the blade to the distal end of the blade, with the blade extending from a joining region at the distal end of the waveguide, wherein a longitudinal axis of the waveguide and the longitudinal axis of the blade intersect at an acute non-zero angle, and wherein the cylindrical shape and part-cylindrical shape have substantially the same radius of curvature, and further comprising a spacer attached directly to a face of the blade with the spacer adapted to contact a stem of an implant to prevent direct contact between said face of the blade and the stem of the implant.

\* \* \* \* \*